United States Patent [19]
Glover

[11] Patent Number: 5,942,655
[45] Date of Patent: Aug. 24, 1999

[54] PROCESS FOR THE REMOVAL OF HEAVY HYDROCARBONACEOUS CO-PRODUCTS FROM A VAPOR EFFLUENT FROM A NORMALLY GASEOUS HYDROCARBON DEHYDROGENATION REACTION ZONE

[75] Inventor: Bryan K. Glover, Algonquin, Ill.

[73] Assignee: UOP LLC, Des Plaines, Ill.

[21] Appl. No.: 08/925,686

[22] Filed: Sep. 9, 1997

[51] Int. Cl.$^6$ .............................. C07C 7/00; C07C 5/327
[52] U.S. Cl. ........................ 585/809; 585/804; 585/805; 585/807; 585/809; 585/867; 585/655
[58] Field of Search ..................................... 585/804, 805, 585/807, 809, 867, 448, 450, 655

[56] References Cited

U.S. PATENT DOCUMENTS

| | | | |
|---|---|---|---|
| 4,430,517 | 2/1984 | Imai et al. ............................... | 585/444 |
| 5,414,168 | 5/1995 | Scott ........................................... | 585/2 |
| 5,672,804 | 9/1997 | Glover ..................................... | 585/655 |
| 5,849,979 | 12/1998 | Kalnes et al. ............................ | 585/809 |

*Primary Examiner*—Glenn Caldarola
*Assistant Examiner*—Thuan D. Dang
*Attorney, Agent, or Firm*—Thomas K. McBride; John G. Tolomei; John G. Cutts, Jr.

[57] ABSTRACT

A process for the removal of trace quantities of polynuclear aromatic compounds from the vapor effluent of a hydrocarbon dehydrogenation zone containing normally gaseous olefinic hydrocarbons, trace mononuclear aromatic compounds and trace polynuclear aromatic compounds by contacting the vapor effluent of a hydrocarbon dehydrogenation zone with a lean liquid absorption stream comprising at least one alkylated mononuclear aromatic compound to absorb at least a portion of the trace mononuclear aromatic compounds and the trace polynuclear aromatic compounds to produce a rich liquid absorption stream and a gaseous olefin-containing hydrocarbon stream having a reduced concentration of mononuclear aromatic compounds and polynuclear aromatic compounds. The rich liquid absorption stream is separated to produce a stream rich in mononuclear aromatic compounds, a stream rich in alkylated mononuclear aromatic compounds and a stream comprising polynuclear aromatic compounds. At least a portion of the stream rich in mononuclear aromatic compounds is alkylated with indigenous olefins to provide at least a portion of the lean liquid absorption stream.

11 Claims, 1 Drawing Sheet

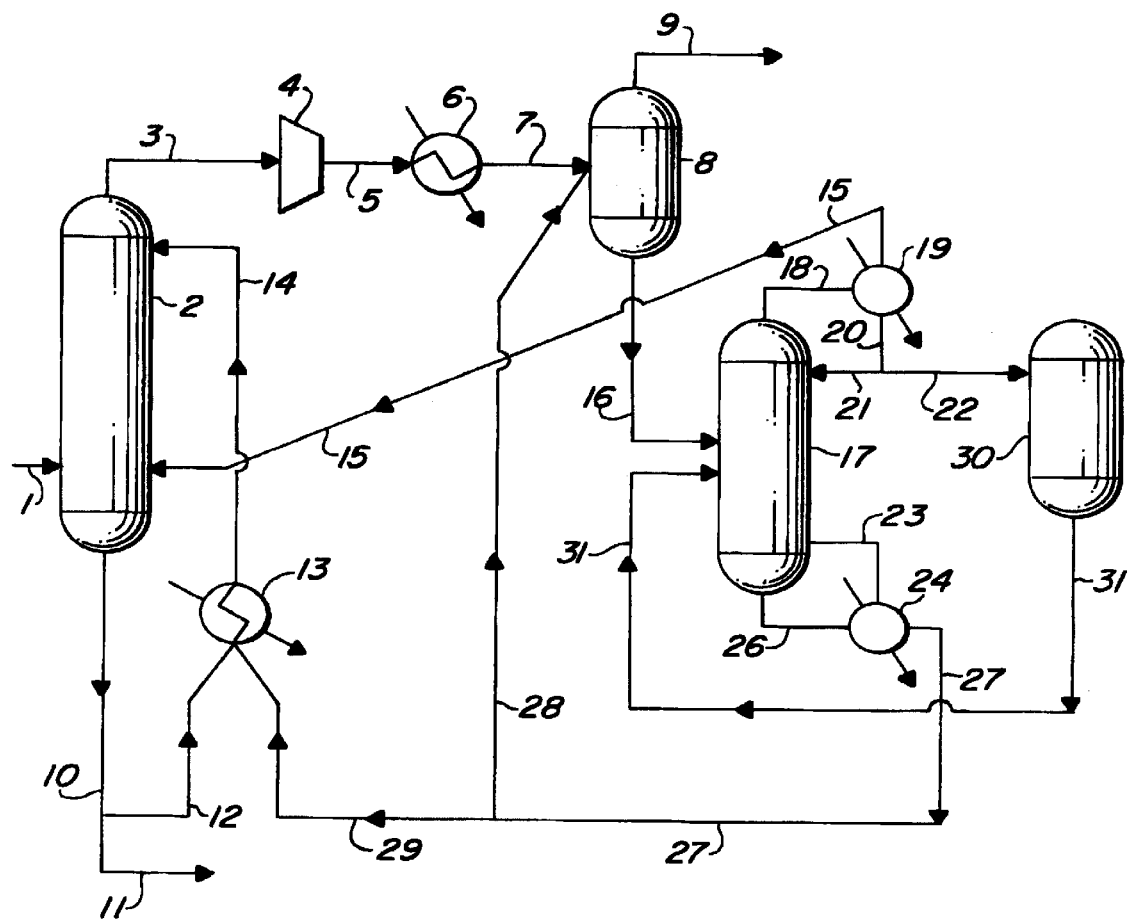

PROCESS FOR THE REMOVAL OF HEAVY HYDROCARBONACEOUS CO-PRODUCTS FROM A VAPOR EFFLUENT FROM A NORMALLY GASEOUS HYDROCARBON DEHYDROGENATION REACTION ZONE

FIELD OF THE INVENTION

The field of art to which this invention pertains is the removal and recovery of heavy hydrocarbonaceous co-products including mononuclear and polynuclear aromatic compounds from the vapor effluent from a normally gaseous hydrocarbon dehydrogenation reaction zone.

BACKGROUND OF THE INVENTION

The dehydrogenation of hydrocarbons is an important commercial hydrocarbon conversion process because of the existing and growing demand for dehydrogenated hydrocarbons for the manufacture of various chemical products such as detergents, high octane gasolines, oxygenated gasoline blending components, pharmaceutical products, plastics, synthetic rubbers and other products which are well known to those skilled in the art. One example of this process is the dehydrogenation of isobutane to produce isobutylene which can be polymerized to provide tackifying agents for adhesives, viscosity-index additives for motor oils and impact-resistant and anti-oxidant additives for plastics. Another example of the growing demand for isobutylene is the production of oxygen-containing gasoline blending components which are being mandated by the government in order to reduce air pollution from automotive emissions.

Those skilled in the art of hydrocarbon conversion processing are well versed in the production of olefins by means of catalytic dehydrogenation of paraffinic hydrocarbons. In addition, many patents have issued which teach and discuss the dehydrogenation of hydrocarbons in general. For example, U.S. Pat. No. 4,430,517 issued to Imai et al discusses a dehydrogenation process and catalyst for use therein.

Despite the fact that the dehydrogenation of paraffinic hydrocarbons is well known, the more widespread usage of this processing technology and greater severity operation of existing commercial facilities has highlighted the problem which occurs in the product recovery section of hydrocarbon dehydrogenation processes. This problem is the result of the co-production of trace quantities of mononuclear aromatic and polynuclear aromatic compounds. The mononuclear aromatic compounds are considered to be an undesired impurity in the desired olefinic hydrocarbon product stream and must be removed. The polynuclear aromatic compounds are not only an undesired impurity, but also present a severe operational problem because when they condense and plate out on the cooler surfaces of the plant there are detrimental results. The deposits of polynuclear aromatic compounds are difficult to remove, they reduce the efficiency of heat exchangers and they may eventually lead to plugging.

Therefore, those skilled in the art of hydrocarbon processing have sought methods to overcome the problem posed by the production of polynuclear aromatic compounds in dehydrogenation production facilities. Previous solutions to this problem have centered on recovering low molecular weight mononuclear aromatic hydrocarbon compounds from the dehydrogenation effluent and recycling these hydrocarbon compounds as a wash solvent. A drawback to this technique is that low molecular weight mononuclear aromatic hydrocarbon compounds cannot be easily separated from the normally gaseous hydrocarbon product without using high pressure or low temperature separation. Without high pressure or low temperature separation, significant quantities of wash solvent containing low molecular weight mononuclear aromatic hydrocarbon compounds will be carried forward through the compressor from the wash section thereby adding an additional load to the compressor.

BRIEF SUMMARY OF THE INVENTION

The present invention relates to a process for the removal of trace quantities of polynuclear aromatic compounds from the vapor effluent of a hydrocarbon dehydrogenation zone containing normally gaseous olefinic hydrocarbons and trace quantities of mononuclear and polynuclear aromatic compounds.

The usefulness of the low molecular weight mononuclear aromatic wash solvent is greatly enhanced by alkylating the wash solvent with olefins which are available in the dehydrogenation process. The resulting higher molecular weight mononuclear aromatic solvent is more easily separated from the normally gaseous hydrocarbons. The process of the present invention provides a facile and economical solution to the problem of the co-production of mononuclear and polynuclear aromatic compounds in a dehydrogenation plant.

One embodiment of the present invention may be characterized as a process for the removal of trace quantities of polynuclear aromatic compounds from the vapor effluent of a hydrocarbon dehydrogenation zone comprising normally gaseous olefinic hydrocarbons, trace mononuclear aromatic compounds and trace polynuclear aromatic compounds which process comprises: (a) contacting the vapor effluent of a hydrocarbon dehydrogenation zone with a lean liquid absorption stream comprising at least one alkylated mononuclear aromatic compound to absorb at least a portion of the trace mononuclear aromatic compounds and the trace polynuclear aromatic compounds to produce a rich liquid absorption stream and a gaseous olefin-containing hydrocarbon stream having a reduced concentration of mononuclear aromatic compounds and polynuclear aromatic compounds; (b) recovering the gaseous olefin-containing hydrocarbon stream having a reduced concentration of mononuclear aromatic compounds and polynuclear aromatic compounds; (c) separating the rich liquid absorption stream from step (a) to produce a stream rich in mononuclear aromatic compounds, a stream rich in alkylated mononuclear aromatic compounds and a stream comprising polynuclear aromatic compounds; (d) recycling at least a portion of the stream rich in alkylated mononuclear aromatic compounds to step (a) to provide at least a portion of the lean liquid absorption stream; (e) alkylating at least a portion of the gaseous olefin-containing hydrocarbon stream from step (b) with at least a portion of the stream rich in mononuclear aromatic compounds from step (c) in a catalytic alkylation zone to produce the alkylated mononuclear aromatic compound; and (f) recovering the stream comprising polynuclear aromatic compounds.

Other embodiments of the present invention encompass further details such as preferred absorption solutions, alkylation catalysts and operating conditions.

The process of the present invention provides the advantages of using an indigenous, undesirable co-product, i.e., mononuclear aromatic compounds which are alkylated with an olefin, to serve as a liquid absorption stream for the purification of normally gaseous olefinic hydrocarbons by the separation of trace quantities of polynuclear aromatic compounds from the olefinic hydrocarbons.

BRIEF DESCRIPTION OF THE DRAWING

The drawing is a simplified process flow diagram of a preferred embodiment of the present invention. The above-described drawing is intended to be schematically illustrative of the present invention and is not to be a limitation thereof.

DETAILED DESCRIPTION OF THE INVENTION

The present invention is a process for the removal of trace quantities of polynuclear aromatic compounds from the vapor effluent of a hydrocarbon dehydrogenation zone. The dehydrogenation of paraffinic hydrocarbons is well known to those skilled in the art of hydrocarbon processing.

In the dehydrogenation process, fresh hydrocarbon feed is combined with recycle hydrogen and unconverted hydrocarbons. This forms a reactant stream which is passed through a bed of suitable dehydrogenation catalyst maintained at the proper dehydrogenation conditions such as temperature, pressure and space velocity, and the effluent from the catalytic reaction zone is processed further to yield a stream of olefinic hydrocarbons. In accordance with the present invention, the effluent from the catalytic reaction zone contains unconverted saturated hydrocarbons, olefin hydrocarbons, mononuclear aromatic compounds in an amount from about 100 to about 5,000 wppm and polynuclear aromatic compounds in an amount from about 50 to about 500 wppm.

In accordance with the present invention, the dehydrogenation reaction zone effluent is preferably cooled to a temperature in the range from about 50° F. (10° C.) to about 150° F. (65° C.) and contacted in a contacting zone with a lean liquid absorption stream containing at least one alkylated mononuclear aromatic compound in order to separate and recover the trace quantities of polynuclear aromatic compounds which are contained in the dehydrogenation reaction zone effluent. The resulting scrubbed dehydrogenation reaction zone effluent may then be compressed, cooled, subjected to cryogenic refrigeration, treated for chloride removal, treated for water removal or fractionated, for example.

In another preferred embodiment, after the effluent from the hydrocarbon dehydrogenation zone has been contacted with the lean liquid absorption liquid, the resulting gaseous olefinic hydrocarbon stream is compressed to a pressure in the range from about 30 psig (207 kPa gauge) to about 200 psig (1379 kPa gauge), and cooled to a temperature in the range from about 100° F. (38° C.) to about 150° F. (65° C.), and introduced into a vapor-liquid separation zone. A liquid stream is removed from the vapor-liquid separation zone and recovered. The vapor stream leaving the vapor-liquid separation zone is essentially free of polynuclear aromatic compounds and has a greatly reduced level of mononuclear aromatic compounds. Preferably, the vapor stream contains less than about 10 wppm mononuclear aromatic compounds and less than about 1 wppm polynuclear aromatic compounds. The alkylated mononuclear aromatic compounds which are utilized in the lean liquid absorption stream are preferably produced by reacting low molecular weight mononuclear aromatic compounds such as benzene, toluene and xylene, for example, with an olefinic hydrocarbon resulting from the dehydrogenation zone in an alkylation reaction zone. The olefinic hydrocarbon is preferably propylene or butylene and will be dictated by the feed to the dehydrogenation zone. The preferred alkylated mononuclear aromatic compounds have nine or more carbon atoms per molecule.

In one embodiment of the present invention, a slipstream of propylene and a slipstream of low molecular weight mononuclear aromatic compounds with the aromatic compounds in stoichiometric excess to propylene is passed into an alkylation reactor containing an alkylation catalyst. Generally, the feed to the reactor is in a liquid phase, at a temperature between about 150 and about 250° C. and at a pressure between about 28 and about 70 atmospheres. Although the catalyst may move through the reactor in a moving bed, more typically the catalyst is in the reactor in a fixed bed. The alkylation reactions are principally exothermic, and so the temperature of the reaction mixture rises as it passes through the alkylation reactor. The space velocity of the propylene (olefin) may range from about 0.01 to about 0.05 gram-mole of olefin per gram of catalyst per hour. The mole ratio of aromatic to the olefin is preferably within the broad range of about 3:1 to about 50:1.

A suitable catalyst for the present invention may be one of a broad class of aluminosilicate molecular sieves known as zeolites. The zeolitic molecular sieves suitable for use in the present invention are crystalline aluminosilicates which in the calcined form represented by the general formula:

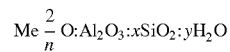

where Me is a cation, n is the valence of the cation, x has a value from about 5 to about 100 and y has a value from about 2 to about 10.

Typical well known zeolites which may be used include Zeolite X, Zeolite Y, Linde Type L, medium pore ZSM-type zeolites such as ZSM-5, mordenite, omega and beta. Detailed descriptions of the above-identified zeolites, as well as others, may be found in D. W. Breck, *Zeolite Molecular Sieves*, John Wiley and Sons, New York 1974, and in other standard references. Preferred zeolites for use in the present invention are rare earth exchanged Y and steam stabilized Y zeolites as disclosed in U.S. Pat. No. 4,459,426 and zeolite beta as disclosed in U.S. Pat. No. 5,081,323.

DETAILED DESCRIPTION OF THE DRAWING

With reference now to the drawing, a vapor effluent from a hydrocarbon dehydrogenation zone containing normally gaseous olefinic hydrocarbons, trace low molecular weight mononuclear aromatic compounds and trace polynuclear aromatic compounds is introduced into the process via conduit 1 and enters absorption zone 2. The vapor effluent is contacted in absorption zone 2 with a hereinafter-described lean absorption solution introduced via conduit 14 in order to remove essentially all of the trace low molecular weight mononuclear aromatic compounds and the trace polynuclear aromatic compounds. A resulting vapor stream having a reduced level of mononuclear and polynuclear aromatic compounds is removed from absorption zone 2 via conduit 3 and introduced into compressor 4. The resulting compressed gas is removed from compressor 4 via conduit 5 and is cooled in heat exchanger 6. A resulting two-phase stream is removed from heat exchanger 6 via conduit 7 and introduced into vapor-liquid separator 8. A vapor stream containing normally gaseous olefinic hydrocarbons is removed from vapor-liquid separator 8 via conduit 9 and recovered. A condensed liquid stream is removed from vapor-liquid separator 8 via conduit 16 and introduced into fractionation zone 17. A rich liquid absorption stream is removed from absorption zone 2 via conduit 10 and at least a major portion is introduced via conduit 12 into heat exchanger 13 and the resulting cooled effluent is recycled via conduit 14 into absorption zone 2. A slipstream of a rich liquid absorption stream containing polynuclear aromatic compounds is removed from the process via conduits 10 and 11. A vapor stream is removed from fractionation zone 17 via conduit 18 and is partially condensed in heat exchanger 19. A resulting gaseous stream is removed from the overhead of fractionation zone 17 via conduit 15 and introduced into absorption zone 2. A reflux stream is introduced into the overhead of fractionation zone 17 via conduits 20 and 21. A net liquid overhead stream containing mononuclear aromatic compounds and normally gaseous olefinic hydrocarbons is removed from fractionation zone 17 via conduits 20 and 22 and introduced into catalytic alkylation zone 30. The resulting effluent from catalytic alkylation zone 30 is transported via conduit 31 and introduced into fractionation zone 17. A bottoms stream from fractionation zone 17 is removed via conduit 26 and reboiled in heat-exchanger 24 and a resulting vapor is introduced into fractionation zone 17 via conduit 23. A net liquid stream from fractionation zone 17 is transported via conduit 27 and a portion thereof is further transported via conduit 29 and introduced into heat-exchanger 13. The resulting effluent from heat-exchanger 13 is transported via conduit 14 and introduced into absorption zone 2 as described hereinabove. Another portion of the net bottoms liquid stream from fractionation zone 17 is transported via conduits 27 and 28 and introduced into vapor-liquid separator 8.

The process of the present invention is further demonstrated by the following illustrative embodiment. This illustrative embodiment is, however, not presented to unduly limit the process of this invention, but to further illustrate the advantages of the hereinabove-described embodiment. The following data were not obtained by the actual performance of the present invention, but are considered prospective and reasonably illustrative of the expected performance of the invention.

ILLUSTRATIVE EMBODIMENT

An effluent from a propane-isobutane dehydrogenation zone having the characteristics and flow rate of stream 75 in Table 1 is introduced into a countercurrent absorption zone and is contacted with a lean liquid absorber solution containing combined streams 82 and 88, and having the characteristics and flow rates presented in Table 1. Each of the hereinafter-mentioned streams has the characteristics and flow rates presented in Table 1. A resulting gaseous stream, 79, is removed from the countercurrent absorption zone and is compressed, cooled and subjected to a vapor-liquid separation zone to produce a gaseous stream, 80.

A liquid stream, 84, from the vapor-liquid separator is introduced into a fractionation column along with a stream, 78, which contains alkylated mononuclear aromatic compounds. A net overhead gaseous stream, 85, is removed from the fractionation column and is introduced into the countercurrent absorption zone. A net liquid stream, 77, which contains normally gaseous olefins and mononuclear aromatic compounds is introduced into a solid bed catalytic alkylation zone containing an alkylation catalyst containing alumina and beta zeolite to produce an effluent stream, 78, containing alkylated mononuclear aromatic compounds and which stream is introduced into the fractionation column. A net liquid bottoms stream, 81, is removed from the fractionation column, and at least a portion, identified as stream 88, is cooled and introduced into the countercurrent absorption zone. Another portion of stream 87, identified as stream 89, is introduced into the vapor-liquid separation zone.

A polynuclear aromatic rich stream, 76, is removed from the countercurrent absorption zone and a majority is cooled and recycled to the absorption zone. Another portion of stream 76 identified as stream 83 is removed from the process in order to recover the polynuclear aromatic compounds.

The foegoing description and illustrative embodiment clearly illustrate the advantages encompassed by the method of the present invention and the benefits to be afforded with the use thereof.

TABLE 1

STREAM ANALYSIS AND FLOW RATE

| Stream | 75 | 76 | 77 | 78 | 79 | 80 | 81 |
|---|---|---|---|---|---|---|---|
| Mole Flow LBMOL/HR | | | | | | | |
| $H_2$ | 5823.00 | 1.32 | 0.00 | 0.00 | 5823.60 | 5823.00 | 0.00 |
| $C_1$ | 630.00 | 0.54 | 0.00 | 0.00 | 630.31 | 630.00 | 0.00 |
| $C_2$ | 119.00 | 0.47 | 0.01 | 0.01 | 119.32 | 119.00 | 0.00 |
| $C_3=$ | 627.00 | 6.28 | 0.42 | 0.42 | 631.88 | 626.99 | 0.00 |
| $C_3$ | 1205.00 | 13.61 | 1.01 | 1.01 | 1215.78 | 1204.99 | 0.00 |
| $IC_4=$ | 1176.00 | 32.25 | 4.82 | 1.20 | 1200.54 | 1172.35 | 0.00 |
| $IC_4$ | 1300.00 | 30.79 | 4.59 | 4.60 | 1326.54 | 1299.97 | 0.00 |
| Mononuclear aromatic | 7.00 | 25.41 | 12.04 | 8.43 | 9.48 | 3.34 | 1.33 |
| Alkylated mononuclear aromatic | 0.00 | 1684.02 | 0.25 | 3.86 | 24.53 | 0.78 | 54.75 |
| Polynuclear aromatic | 0.1 | 213.661 | 0.00001 | 0.00001 | 0.10576 | 0.00103 | 0.20776 |

| Stream | 82 | 83 | 84 | 85 | 88 | 89 |
|---|---|---|---|---|---|---|
| Mole Flow LBMOL/HR | | | | | | |
| $H_2$ | 1.31 | 0.01 | 0.69 | 0.60 | 0.00 | 0.00 |
| $C_1$ | 0.54 | 0.00 | 0.32 | 0.32 | 0.00 | 0.00 |
| $C_2$ | 0.46 | 0.00 | 0.32 | 0.32 | 0.00 | 0.00 |
| $C_3=$ | 6.25 | 0.03 | 4.89 | 4.89 | 0.00 | 0.00 |
| $C_3$ | 13.55 | 0.06 | 10.80 | 10.80 | 0.00 | 0.00 |
| $IC_4=$ | 32.12 | 0.13 | 28.20 | 24.59 | 0.00 | 0.00 |
| $IC_4$ | 30.66 | 0.13 | 26.59 | 26.59 | 0.00 | 0.00 |
| Mononuclear aromatic | 25.31 | 0.11 | 6.81 | 1.87 | 0.67 | 0.67 |
| Alkylated mononuclear aromatic | 1677.02 | 7.00 | 51.15 | 0.01 | 27.38 | 27.38 |
| Polynuclear aromatic | 212.772 | 0.88863 | 0.20776 | 6E−08 | 0.10388 | 0.10388 |

What is claimed:

1. A process for the removal of trace quantities of polynuclear aromatic compounds from the vapor effluent of a hydrocarbon dehydrogenation zone comprising normally gaseous olefinic hydrocarbons, trace mononuclear aromatic compounds and trace polynuclear aromatic compounds which process comprises:

a) contacting said vapor effluent of a hydrocarbon dehydrogenation zone with a lean liquid absorption stream comprising at least one alkylated mononuclear aromatic compound to absorb at least a portion of said trace mononuclear aromatic compounds and said trace polynuclear aromatic compounds to produce a rich liquid absorption stream and a gaseous olefin-containing hydrocarbon stream having a reduced concentration of mononuclear aromatic compounds and polynuclear aromatic compounds;

b) recovering said gaseous olefin-containing hydrocarbon stream having a reduced concentration of mononuclear aromatic compounds and polynuclear aromatic compounds;

c) separating said rich liquid absorption stream from step (a) to produce a stream rich in mononuclear aromatic compounds, a stream rich in alkylated mononuclear aromatic compounds and a stream comprising polynuclear aromatic compounds;

d) recycling at least a portion of said stream rich in alkylated mononuclear aromatic compounds to step (a) to provide at least a portion of said lean liquid absorption stream;

e) alkylating at least a portion of said gaseous olefin-containing hydrocarbon stream from step (b) with at least a portion of said stream rich in mononuclear aromatic compounds from step (c) in a catalytic alkylation zone to produce said alkylated mononuclear aromatic compound; and f) recovering said stream comprising polynuclear aromatic compounds.

2. The process of claim 1 wherein said normally gaseous olefinic hydrocarbons are selected from the group consisting of ethylene, propylene and butylene.

3. The process of claim 1 wherein said mononuclear aromatic compounds are selected from the group consisting of benzene, toluene and xylene.

4. The process of claim 1 wherein the trace quantities of polynuclear aromatic compounds are present in said vapor effluent of a dehydrogenation zone in an amount from about 50 to about 500 wppm.

5. The process of claim 1 wherein the trace quantities of mononuclear aromatic compounds are present in said vapor effluent of a dehydrogenation zone in an amount from about 100 to about 5000 wppm.

6. The process of claim 1 wherein said contacting in step (a) is conducted in a countercurrent vapor-liquid extraction zone.

7. The process of claim 1 wherein said gaseous olefin-containing hydrocarbon stream having a reduced concentration of mononuclear aromatic compounds and polynuclear aromatic compounds contains less than about 10 wppm mononuclear aromatic compounds and less than about 1 wppm polynuclear aromatic compounds.

8. The process of claim 1 wherein a net stream of mononuclear aromatic compounds is recovered.

9. The process of claim 1 wherein said alkylated mononuclear aromatic compound has at least nine carbon atoms per molecule.

10. The process of claim 1 wherein said catalytic alkylation zone is operated at conditions including a temperature from about 150° C. and about 250° C., a pressure from about 28 to about 70 atmospheres and a mole ratio of aromatic to olefin from about 3:1 to about 50:1.

11. The process of claim 1 wherein said catalytic alkylation zone contains an alkylation catalyst comprising zeolitic molecular sieves.

\* \* \* \* \*